US010004589B2

(12) United States Patent
Haynes

(10) Patent No.: US 10,004,589 B2
(45) Date of Patent: Jun. 26, 2018

(54) RADIATION SHIELDING IMPLANTS AND METHODS OF USE

(71) Applicant: Daniel F. Haynes, Jonesborough, TN (US)

(72) Inventor: Daniel F. Haynes, Jonesborough, TN (US)

(*) Notice: Subject to any disclaimer, the term of this patent is extended or adjusted under 35 U.S.C. 154(b) by 298 days.

(21) Appl. No.: 14/713,613

(22) Filed: May 15, 2015

(65) Prior Publication Data
US 2015/0327941 A1 Nov. 19, 2015

Related U.S. Application Data

(60) Provisional application No. 61/994,191, filed on May 16, 2014.

(51) Int. Cl.
*A61N 5/10* (2006.01)
*A61F 2/12* (2006.01)
(Continued)

(52) U.S. Cl.
CPC ............... *A61F 2/12* (2013.01); *A61B 19/40* (2013.01); *A61B 90/02* (2016.02); *A61B 90/04* (2016.02); *A61N 5/1015* (2013.01); *A61N 5/1077* (2013.01); *A61B 6/107* (2013.01); *A61B 2019/4045* (2013.01); *A61B 2090/0436* (2016.02); *A61B 2090/0445* (2016.02);
(Continued)

(58) Field of Classification Search
CPC ........... A61F 2/12; A61B 90/02; A61B 90/04; A61B 2090/0436; A61B 2090/0445; A61N 5/1001–5/1027
See application file for complete search history.

(56) References Cited

U.S. PATENT DOCUMENTS 5,190,990 A * 3/1993 Eichmiller ............... G21K 1/10
128/862
6,066,856 A 5/2000 Fishman
(Continued)

OTHER PUBLICATIONS

Biocompatible Materials: US Industry Study with Forecasts to 2010 & 2015, The Freedonia Group (2006), available at http://www.freedoniagroup.com/brochure/21xx/2111smwe.pdf (last accessed May 14, 2015).
(Continued)

*Primary Examiner* — Thaddues Cox
(74) *Attorney, Agent, or Firm* — Dinsmore & Shohl LLP

(57) ABSTRACT

A removable implant having a radiation shield adapted to reduce radiation exposure to one or more secondary radio-sensitive tissues during breast cancer radiation therapy is provided herein, the implant including: a flexible casing having: a base adapted for anchoring the implant to a chest wall of a patient; a cap disposed on the base; and a radiation-absorbing core adapted to absorb at least a portion of cardiac impact zone radiation when compared to a control, wherein the cap encloses the radiation-absorbing core, and wherein the radiation-absorbing core includes: a flexible solid polymer; and a plurality of radiation-absorbing members dispersed throughout the flexible solid polymer. In another embodiment, the implant further includes a breast tissue expander disposed on a top face of the flexible casing of the implant. Methods of use of the described implants are also provided herein.

15 Claims, 11 Drawing Sheets

(51) Int. Cl.
  *A61B 19/00*     (2006.01)
  *A61B 90/00*     (2016.01)
  *A61B 6/10*      (2006.01)

(52) U.S. Cl.
  CPC ............... *A61B 2090/0481* (2016.02); *A61F 2230/0006* (2013.01); *A61F 2250/0003* (2013.01); *A61F 2250/0004* (2013.01); *A61F 2250/0032* (2013.01); *A61F 2250/0059* (2013.01); *A61F 2310/00017* (2013.01); *A61F 2310/00113* (2013.01); *A61F 2310/00137* (2013.01); *A61F 2310/00155* (2013.01); *A61N 2005/1094* (2013.01)

(56) References Cited

U.S. PATENT DOCUMENTS

| | | | |
|---|---|---|---|
| 2006/0224034 A1 | 10/2006 | Reever | |
| 2007/0100355 A1* | 5/2007 | Bonde | A61B 17/12022 606/108 |
| 2014/0336507 A1* | 11/2014 | Cheng | A61N 5/10 600/436 |

OTHER PUBLICATIONS

Shastri, Non-Degradable Biocompatible Polymers in Medicine: Past, Present and Future, Pharmaceutical Biotechnology, 4:331-37 (2003).

\* cited by examiner

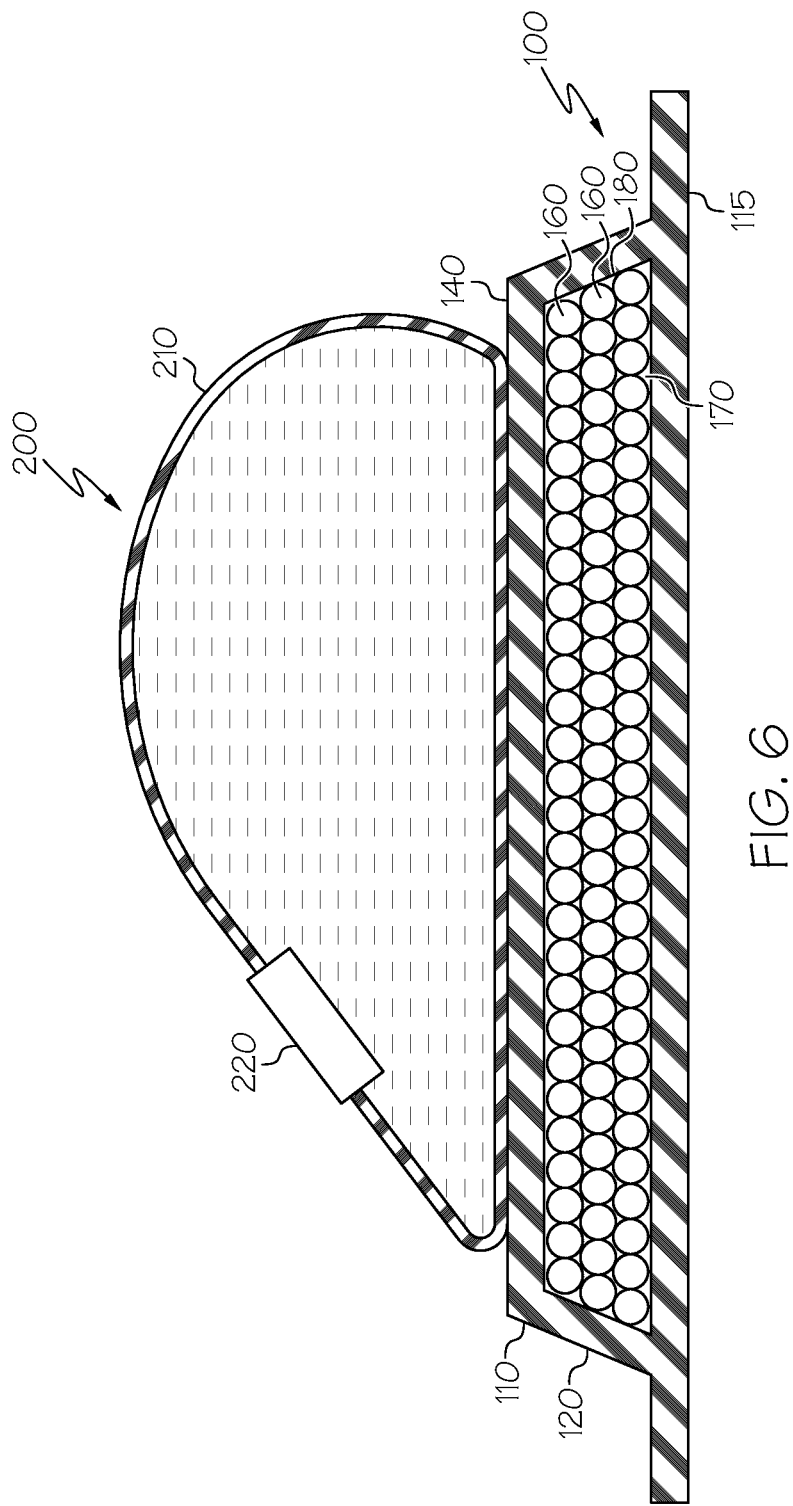

RADIATION SHIELDING IMPLANTS AND METHODS OF USE

RELATED APPLICATION

This application claims the benefit of U.S. Provisional Application No. 61/994,191, filed May 16, 2014, which application is hereby incorporated by reference in its entirety.

FIELD OF THE INVENTION

The presently disclosed subject matter relates to a medical device for use in radiation oncology. Specifically, the present inventive subject matter relates to a removable implant comprising a radiation shield and optional tissue expander adapted to reduce radiation exposure to one or more secondary radio-sensitive tissues during breast cancer radiation therapy associated with breast cancer surgery.

BACKGROUND OF THE INVENTION

Radiation therapy is a recommended course of treatment for many individuals who are diagnosed with breast cancer. Typically, the breast is irradiated after breast-conserving lumpectomies, while the chest wall is irradiated following mastectomy, with or without regional lymph node irradiation. Adjuvant radiation is considered to confer a potential survival advantage and an improvement in local cancer control. Women with node positive breast cancer benefit from comprehensive nodal irradiation, which encompasses larger volumes of normal tissues, including the heart. About four million women in the United States have been treated for breast cancer, the majority having received radiotherapy.

Interestingly, however, while survival data associated with radiation therapy initially indicated that adjuvant radiation conferred a cancer specific survival advantage, no advantage in overall survival was observed. Subsequent increased mortality due to coronary disease and other cardiac conditions has been noted in breast-cancer survivors who have undergone radiation therapy. It is now widely accepted that cardiac structures, including the coronary arteries, are radio-sensitive and vulnerable to damage from radiation that passes through the chest wall.

It has been difficult to quantify the effects of radiation on the heart for many reasons. Until about ten to fifteen years ago, computerized tomography (CT) scanning was not routinely used in radiation planning such that cardiac dose parameters were not available for data-mining and analysis. Further, it often takes many years for radiation-induced damage to cardiac tissue to manifest. By the time data is analyzed for cardiac risk associated with a particular treatment protocol, the treatment protocol may be outdated. According to one seminal study involving 4,456 women treated between 1954 and 1983, researchers found a 1.76-fold higher risk of cardiac disease and a 1.33-fold higher risk of dying from vascular disease among women treated for left-sided breast cancer as compared to those treated for right-sided breast cancer.

Despite advances in radiotherapeutic techniques and the widespread recommendation to radiation oncologists to take precautionary measures, the risk of radiation-related cardiac damage still exists, especially in cases of left-sided breast cancer. For example, in 2008 the radiation plans of 50 patients with left-sided breast cancer and five with right-sided breast cancer were evaluated and outcomes analyzed. Although the radiation dose to all cardiac structures was 1.2 to 2 Gray for right-sided patients, in half of those treated for left-sided cancer, at least part of the heart received a dose higher than 20 Gray. This higher dose has been shown to raise the risk of coronary artery stenosis in the mid- and distal left anterior descending artery, a common site of atherosclerosis leading to heart attack. According to the authors of the study, a 50-year-old woman with no cardiovascular risk factors has a 1.9 percent chance of dying of heart disease before she turns 80, and radiation treatment for breast cancer increases that risk to between 2.4 percent and 3.4 percent, depending on how much radiation exposure the heart receives.

Studies are underway to determine the tolerance doses for radiation that reaches the heart and coronary arteries; however, until formal guidelines are established, efforts to protect the heart and cardiac structures during radiation therapy remain critical to reducing the risk of long-term cardiac damage.

Further, many physicians specializing in women's health issues fear that women will construe the data to mean that it would be preferable to have their breasts removed instead of having lumpectomies, in order to avoid the cardio-damaging effects of radiation. Radiation therapy is generally recommended for women who elect to undergo breast-conserving treatments, such as lumpectomy; whereas, unless a patient is node-positive, radiation therapy is typically avoided when the patient elects a mastectomy. In fact, statistics suggest the fear of radiation damage is indeed influencing operative selection at least in the United States, where the rate of selection of mastectomy over lumpectomy is increasing, in cases where options for treatment exist.

Although most radiation oncologists attempt to avoid radiation exposure to the heart, the heart still receives some of the dose, especially when the left breast is treated. Radiation damage to the linings of blood vessels and scarring of the heart muscle continue to occur. According to a study out of Sweden and Denmark, the records of 2,168 women who had radiation therapy for breast cancer from 1958 to 2001 were analyzed. An alarming 963 of the women experienced major cardiac events sometime after their cancer treatment, defined as infarction or clogged coronary arteries that needed treatment or caused death. Based on inspection of the treatment records, it was determined that the risk began to increase within a few years after radiation exposure, and that the risk continued to increase for at least 20 years. The higher the radiation dose, the higher the risk, and there was some increase in risk at even the lowest level of radiation exposure. With each Gray to which the heart was exposed, the odds of heart attack or another coronary event rose by 7.4 percent. The average dose to the heart over an entire course of radiation therapy was 5 Gray. For an individual woman, the net effect would depend on her baseline initial risk of heart disease and the total radiation dose to the heart.

In accordance with more modern procedures, radiation oncologists report the dose to cardiac structures as less than 5 Gray and closer to 2 Gray. Many radiation oncologists routinely take precautionary measures, including placing external shields in front of the heart and attempting to curve radiation around the chest wall by irradiating from a side perspective rather than straight through the heart and lungs. Other recommended procedures for reducing exposure of secondary radio-sensitive tissues in the lumpectomy context include application of radiotherapy while the patient is in the prone position on a specially adapted table with openings permitting the breasts to fall away from the chest.

Breast brachytherapy is thought to avoid larger doses to secondary tissues and involves either 1) placing multiple catheters into the breast that surround the area where the excised tumor was located, or 2) placing a single catheter in the breast that contains a balloon that inflates once inside the breast, wherein a radioactive pellet is inserted into the catheter(s) on a dosing schedule for a number of days, after which the catheters are removed. Multicatheter brachytherapy is thought to afford the most targeted partial breast irradiation, but has several drawbacks, not the least of which is that radiation continues to reach cardiac tissue. Although the radiation is provided at a severely reduced level, exposure is across a sustained period of time. Further, this method is considered highly technical and is limited to patients with small, early tumors with well-defined borders.

Hence, there remains a need in the art for devices and methods effective for reducing the cardiovascular risk associated with radiotherapy of the chest region.

SUMMARY OF THE INVENTION

Accordingly, provided herein are devices and methods designed to reduce damage to secondary radio-sensitive tissues from radiation therapy adjunctive to breast cancer surgery.

In one embodiment, a removable implant comprising a radiation shield adapted to protect one or more secondary radio-sensitive tissues during breast cancer radiation therapy is provided, the implant comprising: a flexible casing comprising: a base adapted for anchoring the implant to a chest wall of a patient; a cap disposed on the base; and a radiation-absorbing core adapted to absorb at least a portion of cardiac impact zone radiation when compared to a control, wherein the cap encloses the radiation-absorbing core, and wherein the radiation-absorbing core comprises: a flexible solid polymer; and a plurality of radiation-absorbing members dispersed throughout the flexible solid polymer. In another embodiment, the removable implant further comprises a breast tissue expander disposed on a top face of the flexible casing, wherein the breast tissue expander comprises an expandable chamber and a port for injecting the breast tissue expander with an injection fluid.

In another embodiment, a method of minimizing damage to secondary radio-sensitive tissue during post-operative breast cancer radiation therapy of a region of a chest associated with at least one breast is provided, the method comprising: implanting a removable implant according to the present disclosure; irradiating a target region of the chest; removing the removable implant; and optionally reconstructing the breast.

These and other objects, features, embodiments, and advantages will become apparent to those of ordinary skill in the art from a reading of the following detailed description and the appended claims.

BRIEF DESCRIPTION OF THE DRAWINGS

FIG. 4A shows radiation-absorbing members in the form of spheres arranged in a closely-packed face-centered cubic array; FIG. 4B shows a radiation-absorbing core comprising a solid polymer comprising a homogenous distribution of radiation-absorbing members in particulate form; FIG. 4C shown an embodiment wherein the entire implant comprises a flexible polymer comprising a homogenous distribution of radiation-absorbing members in particulate form.

FIG. 6 illustrates a cross-sectional view of an implant comprising a radiation shield and a breast tissue expander.

DETAILED DESCRIPTION OF THE INVENTION

Figure 1:
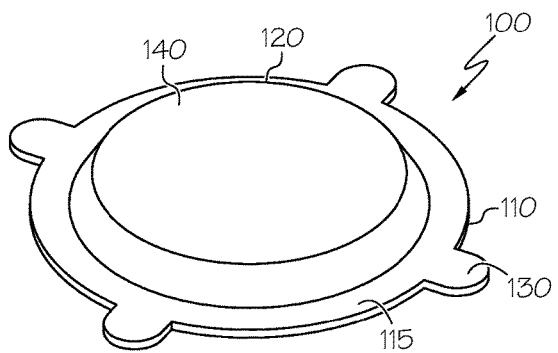
FIG. 1 shows an oblique view of an exemplary implant comprising a radiation shield.

The details of one or more embodiments of the presently-disclosed subject matter are set forth in this document. Modifications to embodiments described in this document, and other embodiments, will be evident to those of ordinary skill in the art after a study of the information provided in this document.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs.

Unless otherwise indicated, all numbers expressing quantities used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The following discussion of the embodiments of the invention directed to removable implants and methods of use are exemplary in nature and are not intended to limit the invention or the applications and uses thereof.

As used herein, the term "secondary radio-sensitive tissues" refers to a tissue that is not the treatment target tissue of radiation therapy, but which may nonetheless receive a dose of radiation incident to radiation therapy of the treatment target tissue. In specific embodiments, the secondary radio-sensitive tissue is selected from a skeletal structure, for example ribs, or sternum; lung tissue; esophageal tissue; skeletal muscle, for example, *pectoralis* muscle; and cardiac structures. In specific embodiments, the secondary radio-sensitive tissue comprises one or more cardiac structures, such as the heart muscle itself and/or vascular structures associated with the heart. In specific embodiments, the cardiac structures comprise the mid- and distal left anterior descending coronary artery.

As used herein, the term "cardiac impact zone" refers to the area under the chest wall occupied by any cardiac tissue that receives radiation through the chest wall during radiotherapy if unshielded. Generally, left-side radiotherapy poses the greatest threat of radiation exposure and, consequently, damage to the underlying cardiac structures.

As used herein, a "flexible" part, material, or implant is a part, material, or implant that is compliant upon the application of pressure from either a surgeon or from pressure incident to placement of the implant in a patient. In certain embodiments, the presently disclosed implants flexibly conform to the surface of the chest wall of a patient once implanted, so that the implant is not unduly uncomfortable to the patient during the period of time it is implanted. In certain embodiments, the implants described herein are flexible such that the surgeon may shape or contour the implant at any time during the implantation process (before or during surgery). Once contoured, the implant will substantially maintain its contoured shape unless sufficient pressure is applied to reshape the implant. The implants described herein are sufficiently flexible to accommodate normal movement of the patient without undue discomfort.

As used herein, the term "face-centered cubic array" refers to an arrangement of radiation-absorbing spheres or beads in square or closely packed arrays. Stacking layers of spheres on top of each other in the radiation absorbing core creates a three dimensional lattice point arrangement represented by a unit cell.

As used herein, the term "perioperative" refers to the three phases of surgery, including the preoperative, intraoperative, and postoperative phases.

Removable Implant Comprising a Radiation Shield

The present inventive subject matter provides devices and methods effective for reducing radiation exposure to secondary radio-sensitive tissues caused by exposure to radiation in association with radiotherapy through the chest wall, such as radiation delivered as an aspect of breast cancer treatment. Typically, node-positive patients and patients electing breast conserving surgery are subjected to radiation therapy. Although radiation therapy has proven effective for increasing survival of breast cancer patients when compared to patients who have not undergone radiation therapy, survival in general remains reduced relative to the general population in large part due to an increase in death from cardiovascular disease. Arterial stenosis and scarring of the heart muscle are associated with exposure to radiation through the chest wall.

Provided herein is a removable implant comprising a radiation shield adapted to reduce radiation exposure to one or more secondary radio-sensitive tissues during breast cancer radiation therapy, the implant comprising: a flexible casing comprising: a base adapted for anchoring the implant to a chest wall of a patient; a cap disposed on the base; and a radiation-absorbing core adapted to absorb at least a portion of cardiac impact zone radiation when compared to a control, wherein the cap encloses the radiation-absorbing core, and wherein the radiation-absorbing core comprises: a flexible solid polymer; and a plurality of radiation-absorbing members dispersed throughout the flexible solid polymer.

The plurality of radiation-absorbing members can be arranged in a variety of configurations within the radiation-absorbing core. In one embodiment, the plurality of radiation-absorbing members are arranged in a face-centered cubic array of spheres or beads. The spheres or beads may be arranged in a closely-packed or square face-centered cubic array. In another embodiment, the plurality of radiation-absorbing members comprise particles that are homogenously dispersed throughout the flexible polymer. In certain embodiments, the particles are nanoparticles of radiation-absorbing material. The arrangement of radiation-absorbing members as either a dispersion of particles or a face-centered cubic array within a flexible polymer imparts flexibility to the implant. The implants disclosed herein may thus be shaped or contoured by the surgeon and/or may conform to the chest wall once implanted in the patient without fracturing the internal structure of the radiation-absorbing core, which might otherwise be the case with more rigid radiation shields, for example, radiation shields comprising planar layers or sheets of radiation-absorbing materials.

The radiation-absorbing members may be formed from a variety of radiation-absorbing materials, including, but not limited to, lead, platinum, tungsten, bismuth, boron, silver, gold, steel, and the like. Other radiation-absorbing materials are known in the art and may be equally suitable for use in the presently disclosed implants. Mixtures and alloys of these and other materials are also suitable for use in the instant implants and methods of use.

The flexible casing can be formed from a variety of flexible, biocompatible materials. In a specific embodiment, the flexible casing comprises silicone elastomer. Other biocompatible materials are known in the art and may be equally suitable for use in the presently disclosed implants. See, for example, *Biocompatible Materials: US Industry Study with Forecasts to* 2010 & 2015, The Freedonia Group (2006), available at http://www.freedoniagroup.com/brochure/21xx/2111smwe.pdf (last accessed May 14, 2015), incorporated herein by reference in its entirety. In certain embodiments, the base comprises suture tabs which enable the device to be conveniently anchored in place in a patient. In other embodiments, one or more exterior faces of the flexible casing comprises a textured surface adapted to mitigate movement of the implant when implanted in a patient. Any of a top face, a bottom face, and/or a side face of the implant may be textured to aid anchoring the implant in place in the patient.

The flexible polymer that encloses the radiation-absorbing members can be formed from a variety of materials, including, but not limited to, thermoplastic urethane (TPU), thermoplastic elastomer (TPE), and silicone. Suitable flexible polymers are disclosed in *Current Pharmaceutical Biotechnology* 4:331-37 (2003); and *Biocompatible Materials: US Industry Study with Forecasts to* 2010 & 2015, The Freedonia Group (2006), available at http://www.freedoniagroup.com/brochure/21xx/2111smwe.pdf (last accessed May 14, 2015), which are incorporated by reference herein in their entirety. In certain embodiments, the flexible polymer is a biocompatible polymer.

The removable implant may be shaped to shield particular structural areas or to shield a maximum region. FIG. 5 shows various embodiments of removable implant shapes, although the skilled artisan will appreciate that other shapes may be similarly useful.

The implants disclosed herein comprise a radiation-absorbing core adapted to absorb at least a portion of cardiac impact zone radiation when compared to a control. In one embodiment, the radiation-absorbing core absorbs at least 10% of cardiac impact zone radiation when compared to a control. In more specific embodiments, the radiation-absorbing core absorbs at least 15-20% of cardiac impact zone radiation, and in very specific embodiments the radiation-absorbing core absorbs between 20% and 50% of the cardiac impact zone radiation when compared to a control.

The presently disclosed implants are adapted to shield secondary radio-sensitive tissue by positioning the implant against a region of the chest wall adjacent a cardiac impact zone after performance of a lumpectomy or mastectomy.

In certain embodiments, the radiation therapy comprises brachytherapy, which is a form of partial breast radiation in which radiation in the form of radioactive pellets or other materials is directed through cannula to circumscribed areas of the breast, for example, to the inside surface and small surrounding area of a cavity formed from excision of a tumor in a lumpectomy procedure. A removable implant in accordance with this embodiment may be smaller and contoured to a portion of the inner surface of such a cavity, in order to reduce exposure of secondary radio-sensitive tissue to radiation therapy to the treatment target tissue.

In other embodiments, the radiation therapy comprises external beam radiation, and the removable implant is of a desired size and shape selected to reduce a maximum amount of radiation exposure to secondary radio-sensitive tissues, in accordance with the condition and treatment plan of the patient.

Another embodiment provides a combination (1) removable implant comprising a radiation shield adapted to reduce radiation exposure to one or more secondary radio-sensitive tissues during breast cancer radiation therapy, and (2) a breast tissue expander. The combination implant/expander comprises a flexible casing comprising a base adapted for anchoring the implant to a chest wall of a patient; a cap disposed on the base; and a radiation-absorbing core adapted to absorb at least a portion of cardiac impact zone radiation when compared to a control, wherein the cap encloses the radiation-absorbing core, and wherein the radiation-absorbing core comprises: a flexible solid polymer; and a plurality of radiation-absorbing members dispersed throughout the flexible solid polymer. The breast tissue expander is disposed on a top face of the flexible casing of the implant and comprises an expandable chamber and a port adapted for injecting the breast tissue expander with an injection fluid, such as saline. The combination implant/expander is particularly useful in shielding a cardiac impact zone after a mastectomy and in association with preparation for reconstructive breast surgery.

In another embodiment, the implant comprises a radiation-absorbing core, wherein the core comprises a plurality of zones, each of said zones comprising a distinct density of radiation-absorbing members, wherein the density of radiation-absorbing members is proportional to the sensitivity of the secondary radio-sensitive tissues to radiation, such that a relatively higher density of radiation-absorbing members is located in a zone that shields tissue comparatively more sensitive to radiation, and a relatively lower density of radiation-absorbing members is located in a zone that shields tissue comparatively less sensitive to radiation. In a more specific embodiment, the plurality of zones comprise concentric zones wherein the center-most zone comprises the relatively higher density of radiation-absorbing members and each concentrically succeeding zone extending toward a perimeter of the radiation-absorbing core comprises a relatively lower density of radiation-absorbing members as compared with a preceding zone. In another embodiment, the plurality of zones comprise eccentric zones. When implanted in a patient, the implant is situated such that the zone having the highest density of radiation-absorbing members overlays at least a portion of the secondary radio-sensitive tissue most sensitive to radiation.

Methods of Use

A method of reducing radiation exposure to secondary radio-sensitive tissue during post-operative breast cancer radiation therapy of a region of a chest associated with at least one breast is provided, the method comprising: implanting the implant as described herein; irradiating a target region of the chest; removing the implant; and optionally reconstructing the breast, wherein the implant absorbs at least a portion of cardiac impact zone radiation when compared to a control, thereby reducing radiation exposure to secondary radio-sensitive tissue. In one embodiment, the implant is implanted adjunctive to breast cancer surgery. After the implant is placed in the patient, the patient may receive radiation therapy substantially immediately, or after some period of time in accordance with the oncology treatment plan for the patient. After the radiation therapy is completed, the implant is removed, at which point breast reconstructive surgery may be carried out. A breast may be reconstructed substantially immediately upon removal of the implant, or at some time subsequent in accordance with needs and desires of the patient.

The secondary radio-sensitive tissue may comprise at least one cardiac structure. Radiation may be administered by application of radiation by external beam therapy or by application of radiation by partial breast radiation, such as by brachytherapy. In one embodiment, the implant is inserted underneath the pectoralis muscle of the chest wall during the perioperative period associated with a mastectomy or a lumpectomy. In another embodiment, the implant is inserted over the pectoralis muscle and under the skin of the chest region during the perioperative period associated with a mastectomy or a lumpectomy. In another embodiment, the implant is inserted into a portion of a contoured inner surface of a cavity remaining after a lumpectomy, during the perioperative period associated with the lumpectomy.

In another embodiment, a method of reducing radiation exposure to secondary radio-sensitive tissue during postoperative breast cancer radiation therapy of a region of a chest associated with at least one breast is provided, the method comprising: implanting a combination removable implant comprising a radiation shield/breast tissue expander as described herein; irradiating a target region of the chest; injecting the breast tissue expander with the injection fluid; removing the combination implant/tissue expander; and optionally reconstructing the breast, wherein the implant absorbs at least a portion of cardiac impact zone radiation when compared to a control, thereby reducing radiation exposure to secondary radio-sensitive tissue. In certain embodiments, the combination removable implant comprising a radiation shield/breast tissue expander is implanted in a procedure adjunctive to a mastectomy and may be implanted under the skin and, in some cases, under the pectoralis muscle perioperative to a mastectomy. The relevant region of the chest is subject to radiotherapy at any time between the mastectomy and complete reconstruction. The combination removable implant comprising a radiation shield/breast tissue expander is removed upon completion of sufficient/desired expansion, and a breast implant may be inserted into the cavity created by the breast tissue expander. The tissue expander may operate according to any known tissue expander in the art. In a specific embodiment, the tissue expander is injected with saline to expand the chamber thereof.

In certain embodiments, irradiating a target region of the chest comprises applying radiation by external beam therapy or brachytherapy.

In another embodiment, use of an implant or a combination implant/tissue expander according to the methods disclosed herein reduces radiation exposure to at least a portion of a pectoralis muscle, such that a condition of the pectoralis muscle is substantially conserved after radiation therapy (compared to the condition of the pectoralis muscle prior to radiation therapy), thereby facilitating breast reconstruction with reduced risk of complications, including complications from capsular contracture. As used herein, the term "condition of a pectoralis muscle" refers to the properties of pliability and expandability of the muscle tissue. When placed over the pectoralis muscle, the implants described herein absorb at least a portion of the radiation directed at the pectoralis muscle, thus reducing damage to the muscle and substantially conserving the condition of the muscle tissue, particularly with respect to pliability and expandability of the muscle. Healthier muscle tissue facilitates breast reconstruction with a reduced risk of complications, including complications due to capsular contracture. Accordingly, use of the implants according to the methods disclosed herein increases the likelihood of a positive aesthetic outcome of breast reconstruction surgery after radiation therapy.

These and other features of the presently disclosed subject matter are further disclosed in the accompanying figures.

Figure 2:
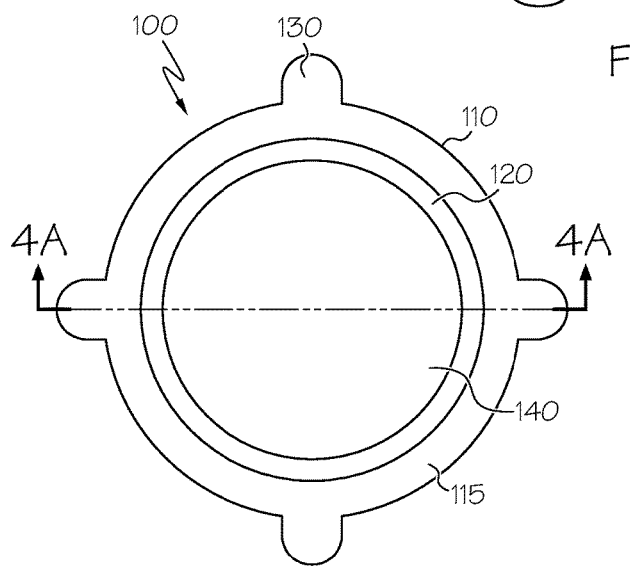
FIG. 2 shows a top view of an exemplary implant comprising a radiation shield.

FIGS. 1 and 2 show an oblique view and a top view, respectively, of an exemplary removable implant comprising a radiation shield 100. The implant 100 comprises a flexible casing 110 comprising a base 115 adapted for anchoring the implant to a chest wall of a patient. In one embodiment, the base 115 comprises one or more suture tabs 130 for anchoring the implant to the chest wall. In another embodiment (not shown), the base may be textured in order to mitigate movement of the implant once placed in the patient. The flexible casing 110 further comprises a cap 120 disposed on the base 115. The cap 120 encloses a radiation-absorbing core (not shown), which is adapted to absorb at least a portion of cardiac impact zone radiation when compared to a control. The implant 100 comprises a top face 140 and a bottom face (not shown). In certain embodiments, any of the external faces of the implant 100 may be textured to mitigate movement of the implant 100 once placed in the patient.

Figure 3:
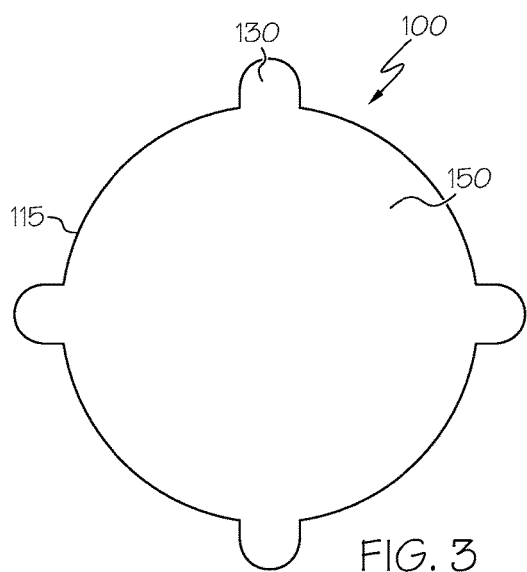
FIG. 3 shows a bottom view of an exemplary implant comprising a radiation shield.

FIG. 3 shows a bottom view of an exemplary removable implant comprising a radiation shield 100. In this view, the bottom face 150 of the base 115 is illustrated. In certain embodiments, the base 115 comprises one or more suture tabs 130 for anchoring the implant to a chest wall of a patient. In another embodiment (not shown), the bottom face 150 of the base 115 may be textured (not shown) in order to mitigate movement of the implant once placed in the patient.

Figure 4A:
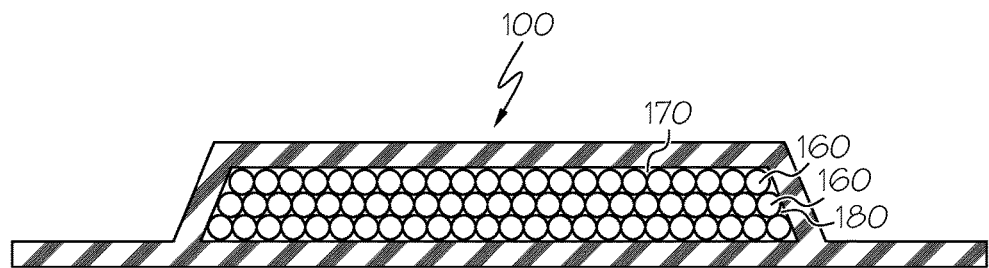
FIGS. 4A-C show cross-sectional views of the implant as depicted in FIG. 2, illustrating various arrangements of radiation-absorbing members that comprise the radiation-absorbing core.
Figure 4B:
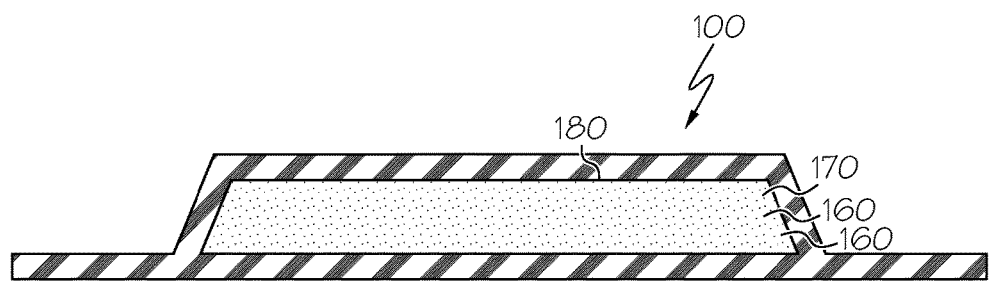
Figure 4C:
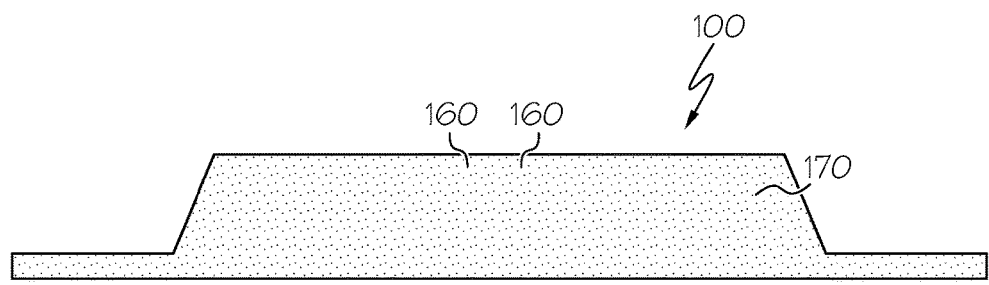
Figure 5A:
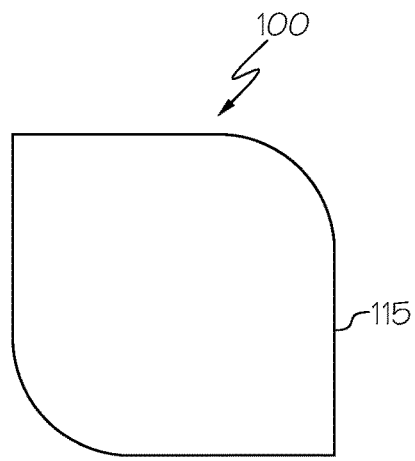
FIGS. 5A-D show various exemplary shapes of the implant, including a rectangle with rounded corners (5A), an oval (5B), a circle (5C), or a rectangle (5D). Suture tabs may optionally be incorporated into any of the embodiments disclosed herein including any of the embodiments shown in FIGS. 5A-D.
Figure 5B:
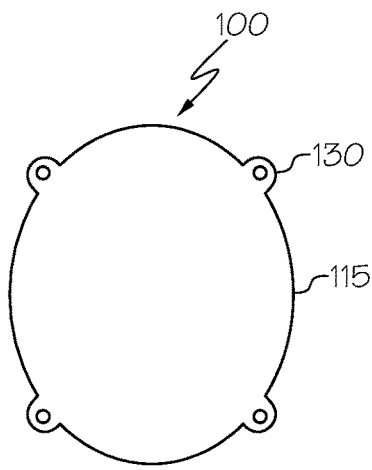
Figure 5C:
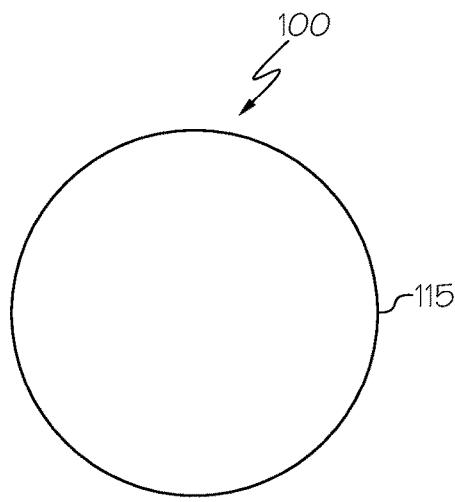
Figure 5D:
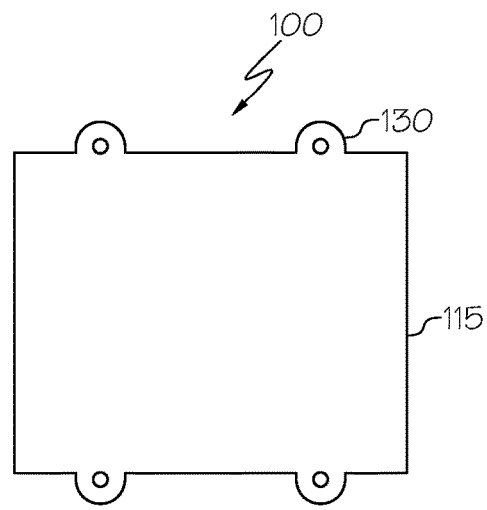

FIGS. 4A-C illustrates cross-sectional views of the removable implant as depicted in FIG. 2, including various exemplary arrangements of radiation-absorbing members 160 within the implant 100. FIG. 4A shows a radiation-absorbing core 180 comprising radiation-absorbing members 160 in the form of spheres arranged in a closely packed face-centered cubic array within the polymer 170. FIG. 4B shows a radiation-absorbing core 180 comprising radiation-absorbing members 160 in the form of particles homogeneously distributed throughout the polymer 170. FIG. 4C shows another embodiment, wherein the entire removable implant 100 is formed from a flexible polymer 170 having radiation-absorbing members 160 in the form of particles homogeneously distributed throughout the entire implant 100. In such an embodiment, radiation attenuation may vary with the thickness of different portions of the implant, for example, a comparatively thinner base may absorb less radiation than a comparatively thicker radiation-absorbing core. In certain embodiments, implants according to any of the embodiments disclosed herein may be substantially planar in form; that is, the base 115 and the cap 120 may be of substantially the same external dimensions. Further, the shape of the cap 120 may be faceted, domed, contoured, or otherwise shaped in any manner that permits enclosure of the radiation-absorbing core 180.

FIGS. 5A-D shows various exemplary shapes of the implant 100, including a base 115 in the shape of a rectangle with rounded corners (5A), an oval (5B), a circle (5C), or a rectangle (5D). Suture tabs 130 may optionally be incorporated into any of the embodiments disclosed herein.

FIG. 6 illustrates a cross-sectional view of a removable implant comprising a radiation shield 100 and a breast tissue expander 200. The breast tissue expander 200 is disposed on a top face 140 of the flexible casing 110 and comprises an expandable chamber 210 and a port 220 for injecting the chamber 210 with an injection fluid, such as saline. The implant 100 contains a radiation absorbing core 180 comprising a polymer 170 and radiation-absorbing members 160 in the form of spheres or beads arranged in a closely-packed face centered cubic array. In alternative embodiments, the radiation-absorbing core 180 may comprise a polymer 170 having radiation-absorbing members 160 in particulate form dispersed homogenously throughout the polymer 170.

Figure 7:
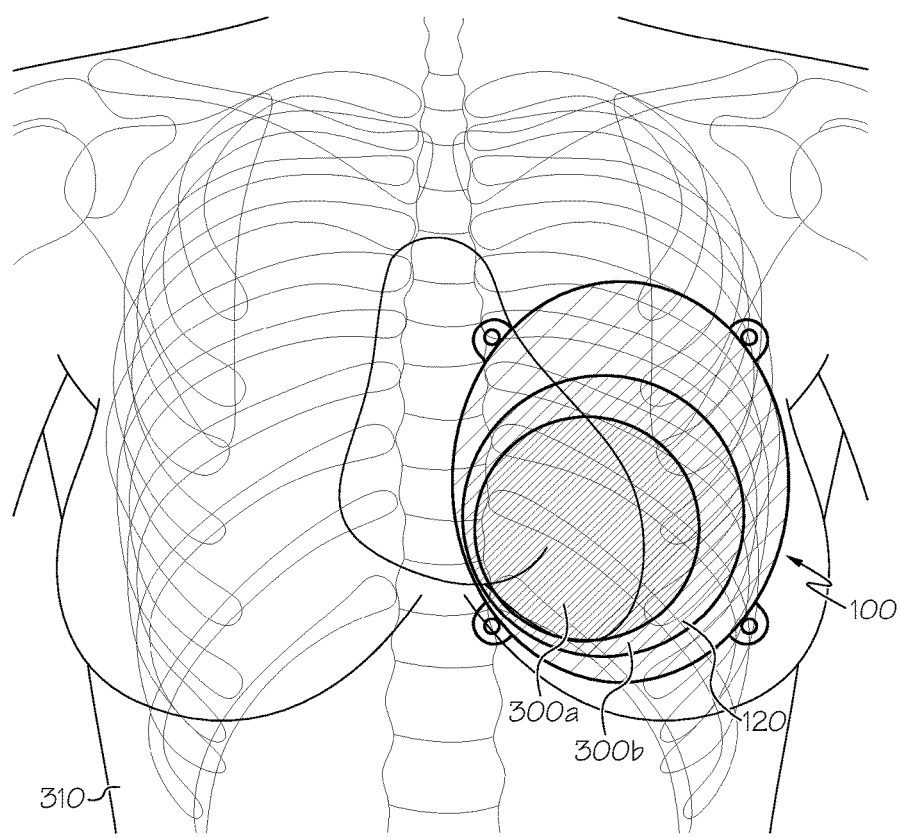
FIG. 7 shows a top view of an implant having a radiation-absorbing core comprising a plurality of zones, wherein each zone comprises a distinct density of radiation-absorbing members.

FIG. 7 illustrates a top view of an implant 100 comprising, inter alia, a cap 120 having disposed therein a radiation-absorbing core comprising a plurality of zones 300, each of said zones comprising a distinct density of radiation-absorbing members (not shown), wherein the zones are designed to provide radiation shielding proportional to the sensitivity of the secondary radio-sensitive tissues underlying the different zones. In the exemplary embodiment of FIG. 7, zone 300a has a comparatively higher density of radiation-absorbing members as compared to zone 300b, which has a comparatively lower density of radiation-absorbing members. The implant 100 is positioned in the patient 310 such that zone 300a overlays the secondary radio-sensitive tissues most sensitive to radiation (for example, cardiac structures), while zone 300b overlays less sensitive radio-sensitive tissues. While the exemplary embodiment illustrates two zones of radiation-absorbing member density 300a and 300b, it is understood that in some embodiments more zones may be appropriate to provide an implant having an enhanced range of radiation absorption, depending on the needs and treatment plan of the patient.

Figure 8:
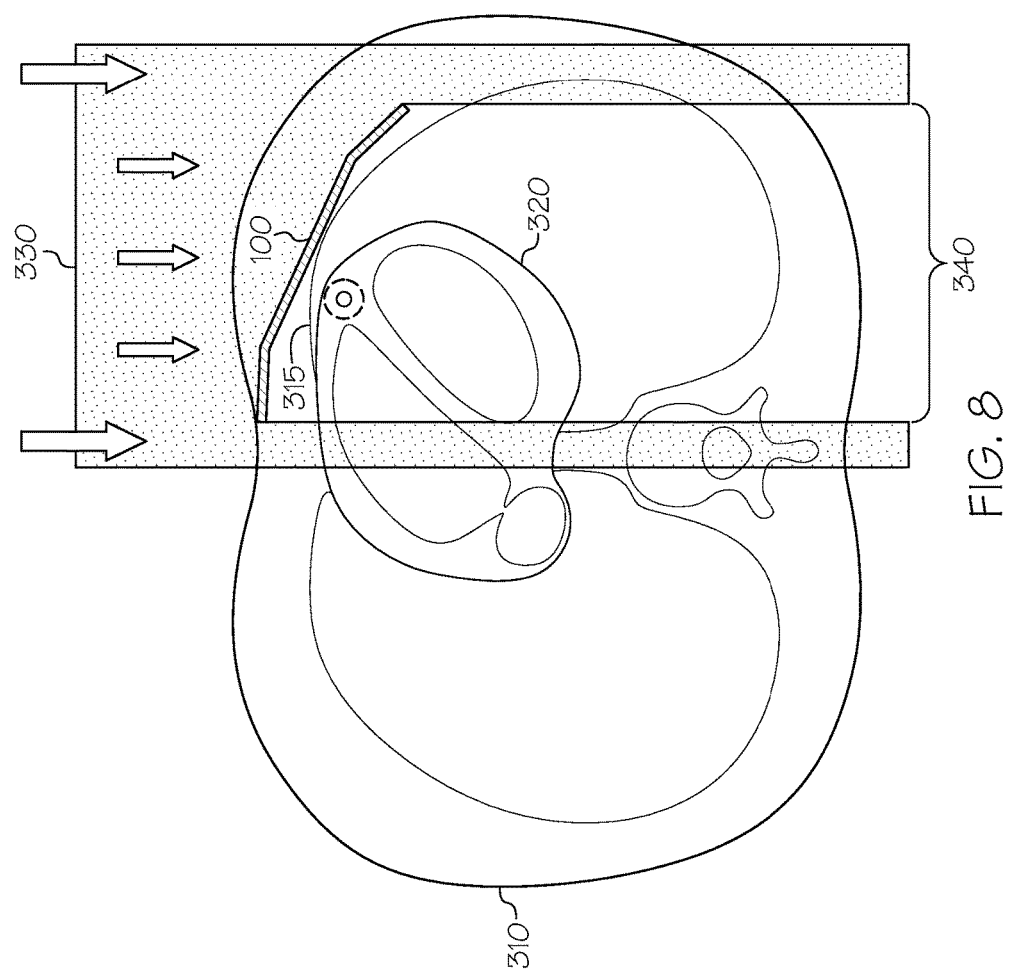
FIG. 8 illustrates a cross-sectional view of the human body, having an implant according to the present disclosure implanted over the chest wall. The figure illustrates the radiation attenuation shadow posterior to the implant, wherein the radiation beam is directed perpendicular to the chest wall.

FIG. 8 illustrates a cross-sectional view of a patient 310, having an implant 100 implanted over the chest wall 315. The removable implant 100 is positioned such that it flexibly conforms to the chest wall 315 and overlays at least a portion of secondary radio-sensitive tissue, including cardiac structures 320. When an external radiation beam 330 is directed at the chest wall 315 at a perpendicular angle to the chest wall 315 (i.e., directly through the chest wall), the implant 100 absorbs at least a portion of the radiation directed at the cardiac impact zone, thus shielding at least a portion of the underlying cardiac structures 320 positioned in the radiation attenuation shadow 340 posterior to the implant 100.

Figure 9:
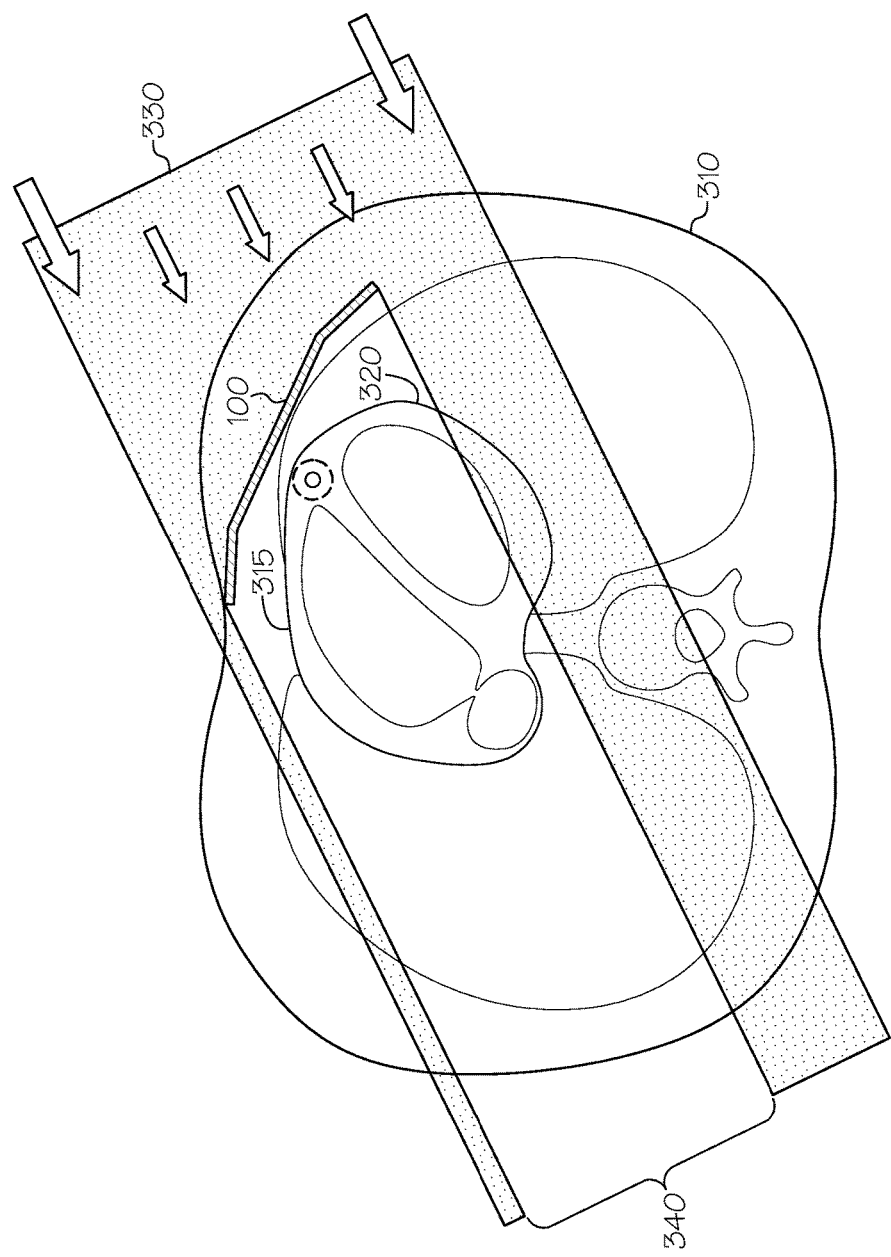
FIG. 9 illustrates a cross-sectional view of the human body, having an implant according to the present disclosure implanted over the chest wall. The figure illustrates the radiation attenuation shadow posterior to the implant, wherein the radiation beam is directed from a side perspective to the chest wall.

FIG. 9 illustrates a cross-sectional view of a patient 310, having an implant 100 implanted over the chest wall 315. The implant 100 is positioned such that it flexibly conforms to the chest wall 315 and overlays at least a portion of secondary radio-sensitive tissue, including cardiac structures 320. When an external radiation beam 330 is directed at a side perspective to the chest wall 315, the implant 100 absorbs at least a portion of the radiation directed at the cardiac impact zone, thus shielding at least a portion of the underlying cardiac structures 320 positioned in the radiation attenuation shadow 340 posterior to the implant 100. As shown in FIG. 9, the side perspective direction of the external radiation beam 330 may be advantageously angled in order to spare as much of the underlying cardiac structures 320 as possible from radiation exposure. The side perspective angle of external radiation beam 330, coupled with use of the implant 100, may shield a comparatively greater portion of the underlying cardiac structure 320 from exposure to radiation, compared to the methods described in FIG. 8, wherein radiation is directed at a perpendicular angle to the chest wall.

Figure 10:
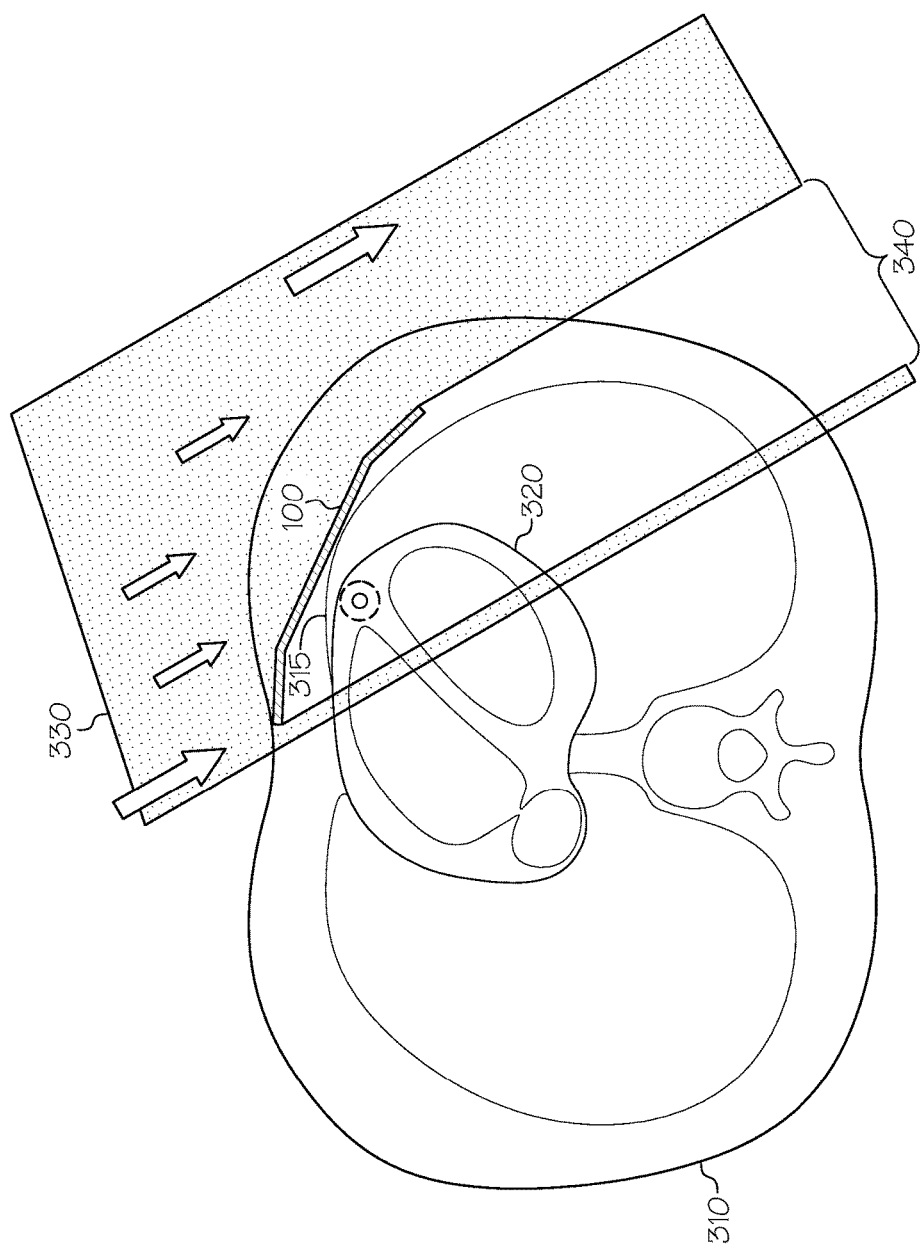
FIG. 10 illustrates a cross-sectional view of the human body, having an implant according to the present disclosure implanted over the chest wall. The figure illustrates the radiation attenuation shadow posterior to the implant, wherein the radiation beam is directed from a side perspective to the chest wall.

FIG. 10 illustrates a cross-sectional view of a patient 310, having an implant 100 implanted over the chest wall 315. The implant 100 is positioned such that it flexibly conforms to the chest wall 315 and overlays at least a portion of secondary radio-sensitive tissue, including cardiac structures 320. When an external radiation beam 330 is directed at a side perspective to the chest wall 315, the implant 100 absorbs at least a portion of the radiation directed at the cardiac impact zone, thus shielding at least a portion of the underlying cardiac structures 320 positioned in the radiation attenuation shadow 340 posterior to the removable implant 100. As shown in FIG. 10, the side perspective direction of the external radiation beam 330 may be advantageously angled in order to spare as much of the underlying cardiac structures 320 as possible from radiation exposure. The side perspective angle of external radiation beam 330, coupled with use of the implant 100, may shield a comparatively greater portion of the underlying cardiac structure 320 from exposure to radiation, compared to the methods described in FIG. 8, wherein radiation is directed at a perpendicular angle to the chest wall.

As illustrated in FIGS. 8 and 9, the presently disclosed implants provide comparatively greater absorption of radiation when radiation contacts the implant at a side perspective angle as compared to a 90° perpendicular angle, since at a side perspective angle, radiation will travel through a tangent thickness of the implant, rather than through the straight dimensional thickness of the implant. For example, if a radiation beam contacts the implant at a 30° side perspective angle, the thickness through which radiation must travel is twice the dimensional thickness of the implant. Accordingly, radiation absorption is increased due to the geometry of the angled beam, as compared to radiation directed at a 90° perpendicular angle.

Figure 11:
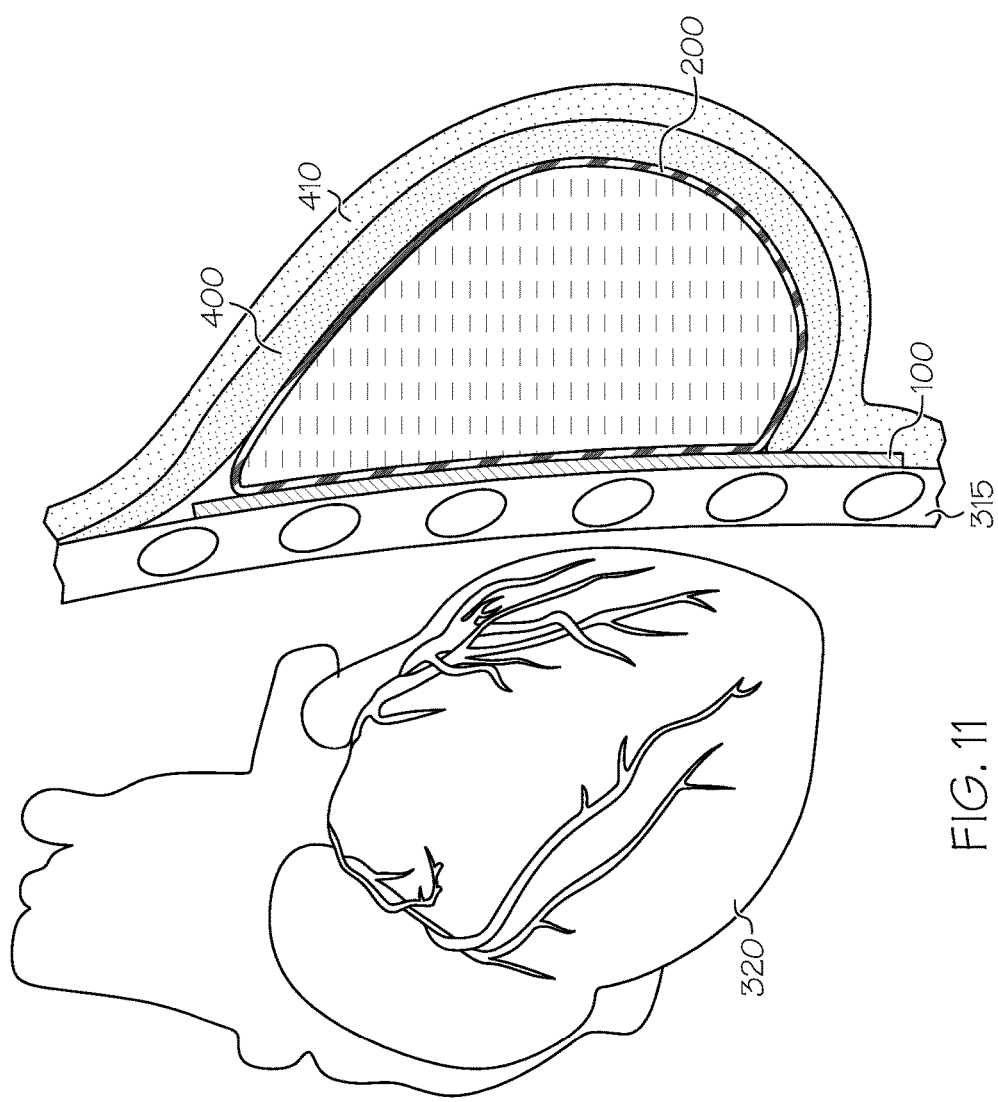
FIG. 11 illustrates a cross-sectional view of an implant comprising a radiation shield and a tissue expander, positioned over the chest wall and under the pectoralis muscle.

FIG. 11 shows a cross-sectional view of an implant comprising a radiation shield 100 and a tissue expander 200, positioned such that it overlays at least a portion of the cardiac structures 320. In this embodiment, the combination implant 100/tissue expander 200 is implanted between the chest wall 315 and the pectoralis muscle 400 of the patient. In certain embodiments not shown, the combination implant 100/tissue expander 200 may alternatively be positioned between the pectoralis muscle 400 and the skin 410 of the patient. The tissue expander 200 can be injected with injection fluid, such as saline, in order to expand the chamber of the tissue expander. In either position, the combination implant 100/tissue expander 200 shields at least a portion of the underlying cardiac structures 320 from radiation while also creating a pocket between the pectoralis muscle 400 and chest wall 315 (or between the pectoralis muscle 400 and the skin 410, if the implant is alternatively positioned) for placement of a breast implant during breast reconstruction surgery.

Figure 12:
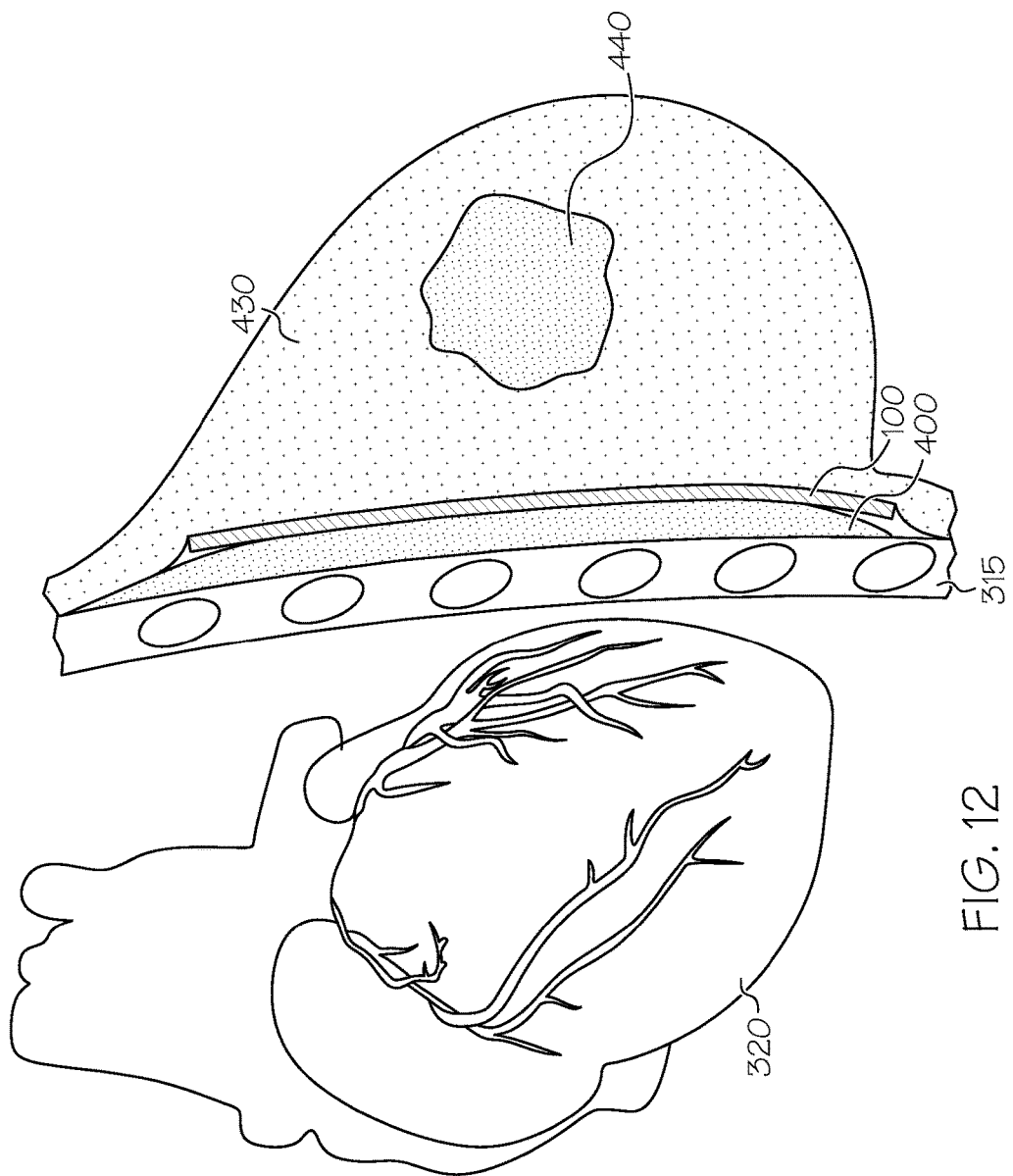
FIG. 12 illustrates a cross-sectional view of an implant comprising a radiation shield and a tissue expander, positioned over the pectoralis muscle.

FIG. 12 shows a cross-sectional view of an implant comprising a radiation shield 100, positioned such that it overlays at least a portion of the cardiac structures 320. In this embodiment, the implant 100 is implanted between the pectoralis muscle 400 and the breast tissue 430 of the patient, who has undergone a lumpectomy procedure which has left a lumpectomy cavity 440. The implant 100 shields at least a portion of the underlying cardiac structures 320 from radiation that will be directed at the tissue in proximity to the lumpectomy cavity 440.

Figure 13:
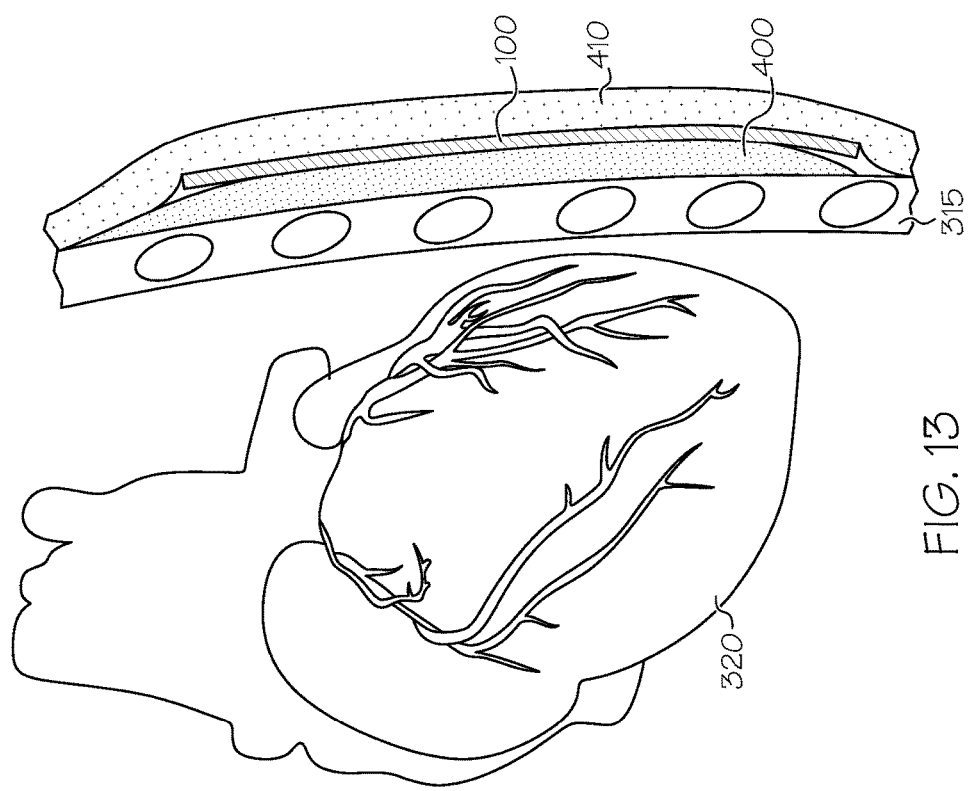
FIG. 13 illustrates a cross-sectional view of an implant positioned over the pectoralis muscle of a patient who has undergone a mastectomy.

FIG. 13 shows a cross-sectional view of a removable implant comprising a radiation shield 100, positioned such that it overlays at least a portion of the cardiac structures 320. In this embodiment, the implant 100 is implanted between the pectoralis muscle 400 and the skin 410 of the patient, who has undergone a mastectomy. The implant 100 shields at least a portion of the underlying cardiac structures 320 from radiation directed at the radiation treatment target area.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

I claim:

1. A removable implant comprising a radiation shield adapted to reduce radiation exposure to one or more secondary radio-sensitive tissues in a patient during breast cancer radiation therapy, the implant comprising:
a flexible casing comprising:
a base adapted for anchoring the implant to a chest wall of a patient;
a cap disposed on the base; and
a radiation-absorbing core adapted to absorb at least a portion of cardiac impact zone radiation when compared to a control,
wherein the cap encloses the radiation-absorbing core, and wherein the radiation-absorbing core comprises:
a flexible solid polymer; and
a plurality of radiation-absorbing members dispersed throughout the flexible solid polymer, wherein the plurality of radiation-absorbing members comprises a face-centered cubic array of radiation-absorbing spheres.

2. The implant according to claim 1, wherein the radiation-absorbing members are formed from material selected from the group consisting of tungsten, bismuth, boron, silver, gold, steel, and combinations thereof.

3. The implant according to claim 1, wherein the flexible casing comprises silicone elastomer.

4. The implant according to claim 1, wherein the flexible solid polymer is selected from the group consisting of thermoplastic polyurethane, thermoplastic elastomer, silicone, and combinations thereof.

5. The implant according to claim 1, wherein the base comprises one or more suture tabs.

6. The implant according to claim 1, wherein one or more exterior faces of the flexible casing comprises a textured surface adapted to mitigate movement of the implant when implanted in a patient.

7. A removable implant comprising a radiation shield adapted to reduce radiation exposure to one or more secondary radio-sensitive tissues in a patient during breast cancer radiation therapy, the implant comprising:
a flexible casing comprising:
a base adapted for anchoring the implant to a chest wall of a patient;
a cap disposed on the base; and
a radiation-absorbing core adapted to absorb at least a portion of cardiac impact zone radiation when compared to a control,
wherein the cap encloses the radiation-absorbing core, and wherein the radiation-absorbing core comprises:
a flexible solid polymer; and
a plurality of radiation-absorbing members dispersed throughout the flexible solid polymer; and
a breast tissue expander disposed on a top face of the flexible casing, wherein the breast tissue expander comprises:
an expandable chamber; and
a port adapted for injecting the breast tissue expander with an injection fluid;
wherein the breast tissue expander is adapted to create a cavity for insertion of a breast implant after radiation therapy.

8. A removable implant comprising a radiation shield adapted to reduce radiation exposure to one or more secondary radio-sensitive tissues in a patient during breast cancer radiation therapy, the implant comprising:
a flexible casing comprising:
a base adapted for anchoring the implant to a chest wall of a patient;
a cap disposed on the base; and
a radiation-absorbing core adapted to absorb at least a portion of cardiac impact zone radiation when compared to a control,
wherein the cap encloses the radiation-absorbing core, and wherein the radiation-absorbing core comprises:
a flexible solid polymer; and
a plurality of radiation-absorbing members dispersed throughout the flexible solid polymer,
wherein the radiation-absorbing core comprises a plurality of zones, each of said zones comprising a distinct density of radiation-absorbing members, wherein the density of radiation-absorbing members is proportional to a sensitivity of the secondary radio-sensitive tissues to radiation, such that a relatively higher density of radiation-absorbing members is located in a zone that shields tissue comparatively more sensitive to radiation, and a relatively lower density of radiation-absorbing members is located in a zone that shields tissue comparatively less sensitive to radiation.

9. The implant according to claim 8, wherein the plurality of zones comprise concentric zones and wherein the centermost zone comprises the relatively higher density of radiation-absorbing members and each concentrically succeeding zone extending toward a perimeter of the radiation-absorbing core comprises a relatively lower density of radiation-absorbing members as compared with a preceding zone.

10. A method of reducing radiation exposure to secondary radio-sensitive tissue during post-operative breast cancer radiation therapy of a region of a chest associated with at least one breast, the method comprising:
(a) implanting a removable implant comprising a radiation shield adapted to reduce radiation exposure to one or more secondary radio-sensitive tissues during breast cancer radiation therapy, the implant comprising:
a flexible casing comprising:
a base adapted for anchoring the implant to a chest wall of a patient;
a cap disposed on the base; and
a radiation-absorbing core adapted to absorb at least a portion of cardiac impact zone radiation when compared to a control,
wherein the cap encloses the radiation-absorbing core, and wherein the radiation-absorbing core comprises:
a flexible solid polymer; and
a plurality of radiation-absorbing members dispersed throughout the flexible solid polymer, wherein the plurality of radiation-absorbing members comprises a face-centered cubic array of radiation-absorbing spheres;
(b) irradiating a target region of the chest;
(c) removing the implant; and
(d) optionally reconstructing the breast,
wherein the implant absorbs at least a portion of cardiac impact zone radiation when compared to a control, thereby reducing radiation exposure to secondary radio-sensitive tissue.

11. The method according to claim 10, wherein the secondary radio-sensitive tissue comprises at least one cardiac structure.

12. The method according to claim 10, wherein irradiating a target region of the chest comprises applying radiation by external beam therapy.

13. The method according to claim 10, wherein irradiating a target region of the chest comprises brachytherapy.

14. The method according to claim 13 wherein the implant is contoured for positioning on an inner surface of a cavity remaining after a lumpectomy.

15. The method according to claim 10, wherein implanting the implant is effectuated during a perioperative period associated with a mastectomy or a lumpectomy.

* * * * *